Figure 1:
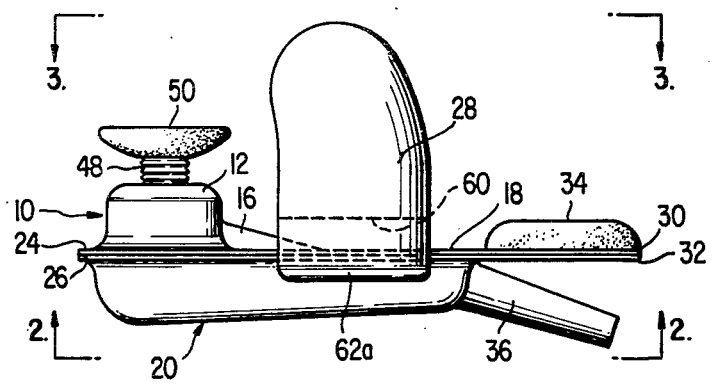

United States Patent [19]

Anderson

[11] 4,194,508
[45] Mar. 25, 1980

[54] EXTERNAL FEMALE URINARY DRAINAGE DEVICE

[76] Inventor: Kenneth E. Anderson, P.O. Box 656, Moline, Ill. 61265

[21] Appl. No.: 891,095

[22] Filed: Mar. 28, 1978

[51] Int. Cl.$^2$ ............................................. A61F 5/44
[52] U.S. Cl. ................................... 128/295; 128/761; 4/144.3
[58] Field of Search ............... 128/2 F, 294, 295; 4/144.1, 144.2, 144.3, 144.4

[56] References Cited

U.S. PATENT DOCUMENTS

| Re. 26,854 | 4/1970 | Giesy | 128/761 |
| 2,483,079 | 9/1949 | Williams | 128/295 |
| 3,072,125 | 1/1963 | O'Brien | 128/295 |
| 3,116,734 | 1/1964 | Teuman | 128/295 |
| 3,194,238 | 7/1965 | Breece, Jr. | 128/295 |
| 3,212,500 | 10/1965 | Bardy | 128/295 |
| 3,340,876 | 9/1967 | Hill | 128/295 |
| 3,347,238 | 10/1967 | Gresham | 128/295 |
| 3,512,185 | 5/1970 | Ellis | 128/295 |
| 3,528,423 | 9/1970 | Lee | 128/295 |
| 3,661,155 | 3/1972 | Lindan | 128/295 |
| 3,703,731 | 11/1972 | Leiser | 4/144.3 |
| 3,722,503 | 3/1973 | Hovick | 128/761 |
| 3,750,648 | 5/1973 | Gleason et al. | 128/761 |
| 3,776,235 | 12/1973 | Ratcliffe et al. | 128/295 |
| 3,900,019 | 8/1975 | Logiadis | 128/295 |
| 4,023,560 | 5/1977 | Cade et al. | 128/295 |
| 4,106,490 | 8/1978 | Spilman | 128/761 |

*Primary Examiner*—Robert W. Michell
*Assistant Examiner*—J. L. Kruter
*Attorney, Agent, or Firm*—Millen & White

[57] ABSTRACT

An externally applied urinary collection and diverting device for incontinent females; including a substantially closed housing having an opening for an ingress conduit with a flexible cup-like diaphragm to fit over the urethral opening to direct urine to the interior of the housing which has a further opening along the length thereof to direct the urine to a collection receptacle without leakage along the vulva area; the housing is of such relatively small size as to be substantially self supporting by entrapment by at least partial covering thereof by the labial folds when positioned for use, and the housing may have attached thereto a perineal pad for similar entrapment thereof in the fourchette area for further support; and with ambulatory females, the housing is shaped to removably and adjustably receive a vaginal insert for still further stabilization and support of the device.

20 Claims, 7 Drawing Figures

U.S. Patent  Mar. 25, 1980  Sheet 1 of 2  4,194,508

4,194,508

EXTERNAL FEMALE URINARY DRAINAGE DEVICE

BACKGROUND OF THE INVENTION

For incontinent females, the collection of involuntary urine discharge is a problem. Such incontinence is often present with geriatric patients and perhaps to a lesser degree in younger females, and even pediatric patients, from various causes, such as a paralysis in lack of control of the sphincter muscle, and others. Prior devices have been developed with this in mind and also to reduce the need or frequency of using a urinary cathether with its attendant discomfort, and to eliminate the need for diaper type receptors. The prior devices have usually included various forms of cap or cup-like members to be placed over the urethral opening for receiving the urine discharge which is directed to a pouch worn by the female or to a discharge collector in cases of bedridden patients. And where such collection devices are to be worn by ambulatory females, whether or not in the category of patients, vaginal inserts have been included for stabilization of the device even though it may be partially stabilized by conforming with the anatomical configurations in the uro-genital areas.

SUMMARY OF THE INVENTION

The present invention is concerned with an external urinary collection device having a pliable diaphragm fitting over the urethral orifice without penetration thereof, for directing discharged urine through a flow tube to the interior of a housing of such relatively small size that it may be fitted and trapped within the labial folds (labia majora and labia minora) for substantial self-support, and the housing is provided with a drainage tube connection generally remote along its length from the flow tube and through which the collected urine may be directed to a collection receptacle for disposal. In addition to the containment of the housing by the labial folds, a perineal pad is extended from the housing for entrapment in the fourchette region for further stabilizing support. This mounting of the device is normally sufficient for bedridden patients but a brief slightly elastic panty arrangement may be employed, if desired, and perhaps particularly if the patient is capable of movement in bed. For ambulatory females and patients, as the case may be, there is provided an optional vaginal insert which may be removably and adjustably attached to the housing intermediate the collection diaphragm and the perineal pad for further support. An object of the present invention is to provide a urinary collection device substantially of the above type which effectively prevents leakage of urine along the uro-genital area, thus to guard against infection and irritation.

Another object of the invention is to provide a collection device substantially of the above type wherein the housing is elongate and closed along the uro-genital area with the collection and drainage tubes relatively oriented to effectively pass the urine through the housing without leakage in normally assumed positions of both bedridden and ambulatory patients.

A further object of the invention is to provide a collection device substantially of the above type wherein the collection flow tube is lightly spring urged outwardly of the housing to correspondingly lightly urge the diaphragm in leakage preventing relationship at the urethral orifice.

A still further object of the invention is to provide a collection device of the above type which is relatively dimensioned to facilitate comfortable anatomical fitting and support along the uro-genital region with permissive bendable adjustment of the orientation of the perineal pad for particular female application.

Figure 2:
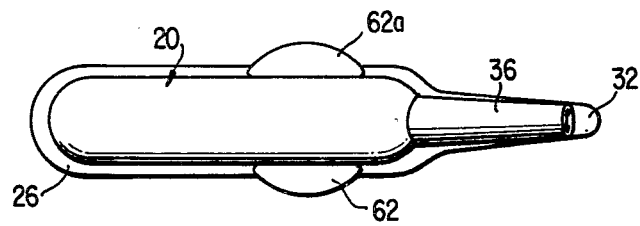
Figure 3:
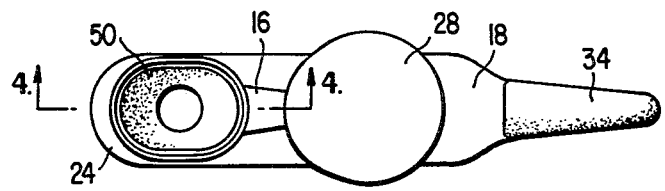
Figure 4:
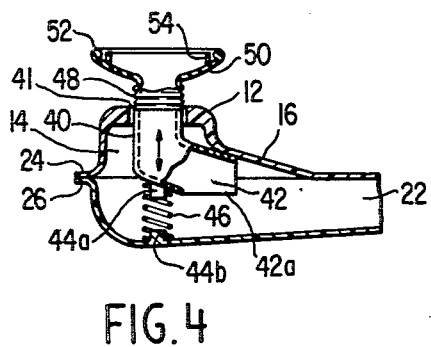
Figure 5:
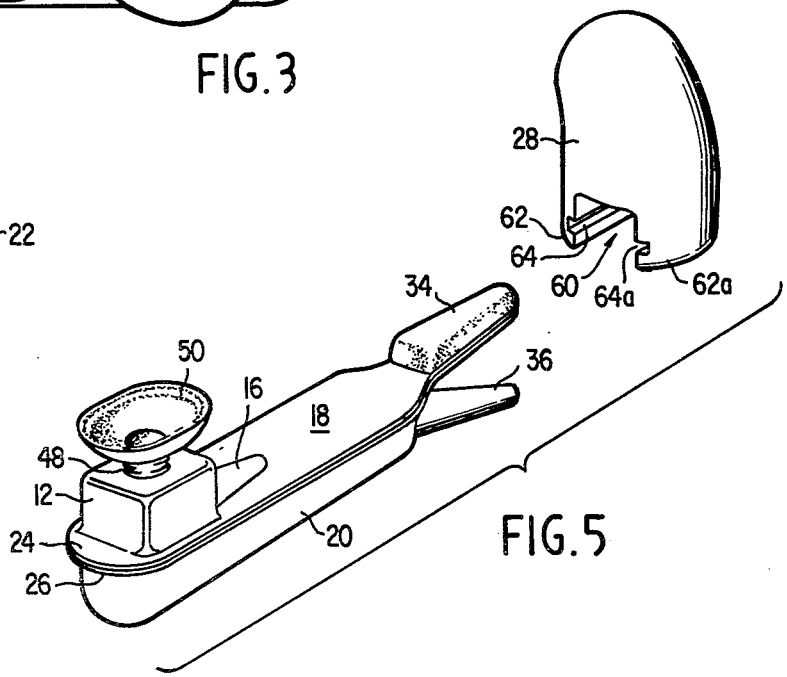
Figure 6:
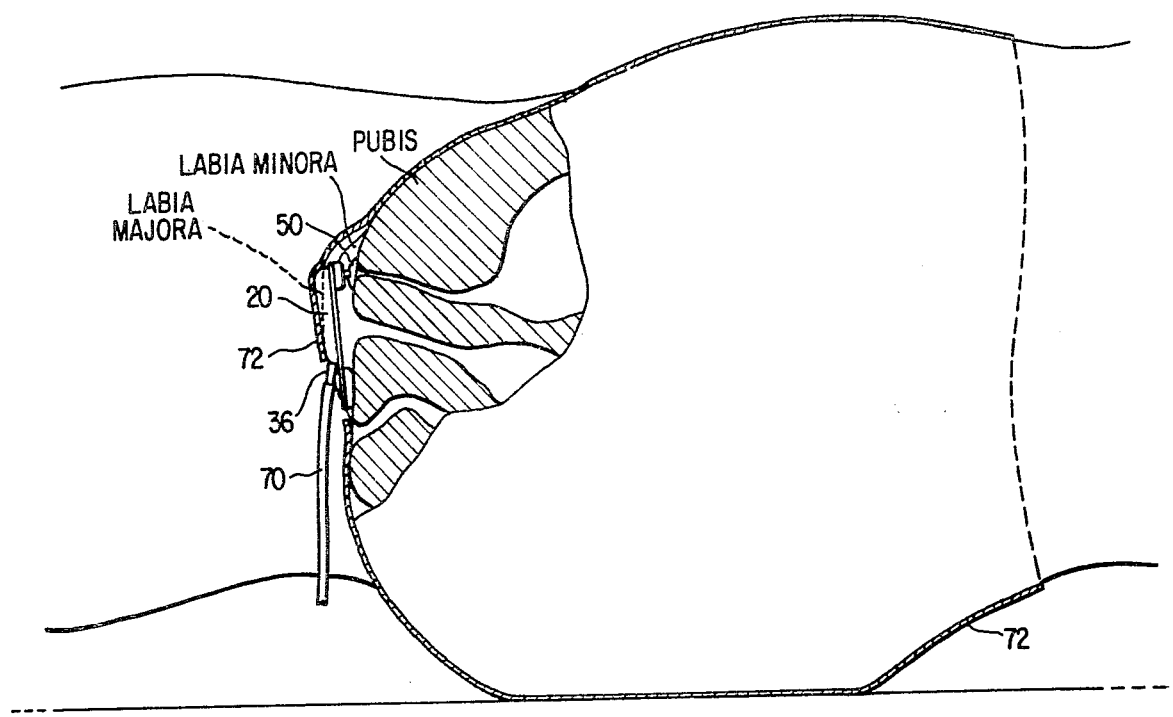
Figure 7:
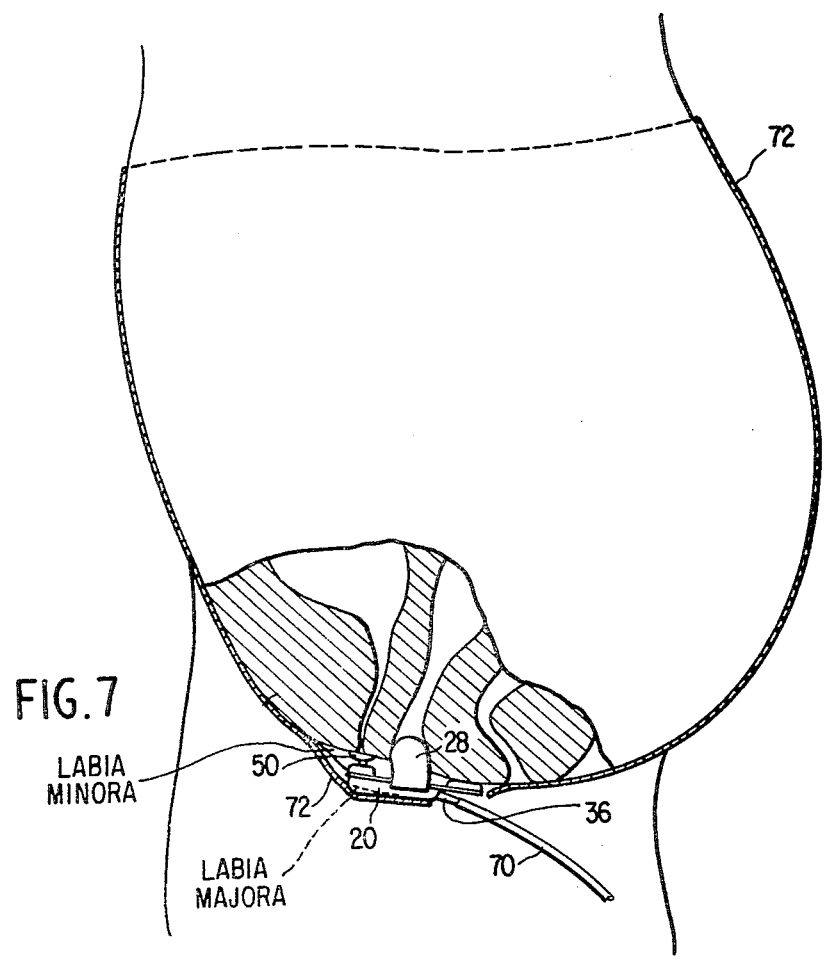

The above and other objects of the invention will in part be obvious and will be hereinafter more fully pointed out in connection with the detail description of the accompanying drawings which, FIG. 1 is a side elevation of the collection device;
FIG. 2 is a bottom plan view of FIG. 1;
FIG. 3 is a top plan view of FIG. 1;
FIG. 4 is a fragmentary section taken on the lines 4—4 of FIG. 3;
FIG. 5 is a prospective view of the device with the vaginal insert separated to illustrate the permissive application, adjustment and removal relative to the collection device;
FIG. 6 is a side view showing a bedridden female, parts in section, with the collection device in position, and
FIG. 7 is a side view, similar to FIG. 6, showing an ambulatory female with the collection device applied.

Before referring to the accompanying drawings, the material of the major parts of the device is selected to possess hypo-allergenic and mucosal non-irritanl characteristics and examples of such materials may be selected from polymers, e.g., polyethylene and polypropylene and polyerinyl plastic materials. For the major parts of the device, the material is semi-rigid permitting localized adjustment as will be pointed out; and for the urethral diaphragm, the material is selected to be very pliable so as to facilitate its conformation with the urethral orifice when in applied position.

With reference to the accompanying drawings, and particularly FIGS. 1, 2 and 3 at this time, the housing includes an upper section 10 having a forward raised portion 12 presenting an internal cavity 14 (FIG. 4) and a rearwardly downwardly inclined narrowing portion 16 merging with a flat rear portion 18. The housing also includes a lower section 20 presenting an interior cavity 22 (FIG. 4) throughout the length thereof. Each of the upper and lower sections have mating peripheral flanges 24, 26, respectively, which are suitably recured together and with nicely rounded peripheral edges. The rearward portions of the mating flanges 24, 26 provide trackways for mounting the vaginal insert 28 which is curved slightly forwardly for secure purchase when in position. The rearwardly extended portion 30 of the flat portion 18 of the upper housing section is narrowed to conform and mate with a similarly shaped rearward extension 32 of the lower housing section, both extensions 30, 32 being suitably secured together and carrying a similarly shaped perineal pad 34. A drainage nipple 36 communicates with the rear end of the housing and is inclined downwardly relative to the pad 34.

At the forward end of the housing, there is provided an ingress flow tube within the cavity 14. This flow tube includes a conduit portion 40 extending through an opening 41 in the top of the raised portion 12 and a rearwardly extending branch conduit 42 opening rearwardly into the cavity 22 and loosely oriented in position by the interior configuration of the portion 16 of the upper housing section. Lugs 44a, 44b in opposition to one another, one on the flow tube bend and the other on the housing section 20, respectively, center a light spring 46 tending to lightly urge the flow tube outwardly of the cavity 14. The outer end of the conduit portion 40 is attached to a bellows section 48 which, in turn, is connected to an upwardly concave urethral diaphragm 50 of longitudinal oval shape with an exterior peripheral smooth lip 52 and an internal continuous flexible lip or skirt 54, both lips being for effective sealing aroung the urethral orifice when positioned for use.

While the vaginal insert 28 is shown assembled in FIGS 1, 2 and 3, references is made to FIG. 5 to illustrate its removability and adjustability. The outer end of the insert is provided with a transverse groove 60 on a depth sufficient to clear the perineal pad 34 when assembled with the collection device. The groove 60 presents legs 62, 62a in which there are transversely extending internal recesses 64, 64a forming trackways snugly receiving the longitudinal tracks presented by sides of the mating flanges 24, 26. Thus, the vaginal insert may be moved toward the collection device, as seen in FIG. 5, with the groove clearing the pad 34 so that the recesses engage the tracks for attaching the insert to the collection device. And when so mounted, there is permissive relative sliding adjustment between the collection device and the insert for fitting the combination to a particular female.

For understanding of the application of the collection device and positioning thereof anatomically to a female in the uro-genital region, reference is made to FIGS. 6 and 7. In FIG. 6, the female is illustrated in prone or bedridden position. To apply the collection device, an attendant or patient, if of well being, will spread apart the labia majora and labia minora, thus exposing the urethra and genital areas in which the collection device is placed with the diaphragm 50 positioned around the urethral orifice and with the perineal pad 34 snugged in the fourchette area. The narrow housing extensions 30, 32 may be bent adjacent the inner end of the perineal pad for proper positioning thereof in the fourchette region to be snuggly trapped therein. Also, allowing the vulva to close, the labial folds will engage around the housing, including the flange portions thereof, to a greater or lesser degree, depending upon the muscle toning and any prolapsed condition in this area of patients of different ages. However, when thusly trapped, the light spring 46 and resiliency of the bellows 48 tend to lightly urge the lips 52, 54 into sealing and non-leaking engagement around the urethral orifice and the bellows also permits slight angular orientation to assist in perfecting the seal. In addition, the very pliable nature of the material of the diaphragm and the bellows further aid in affording a conforming surface contact for sealing purposes with minimal discomfort. In this position of the patient, it will be noted that the conduit portion 42 of the ingress flow tube is oriented rearwardly and downwardly of the housing to encourage flow of discharged urine along the housing and with egress through the drainage nipple 36 to which is attached a tube 70 in turn directed to a collection receptacle for disposal of the discharged urine. Further, the opening 41 through which the conduit portion 40 extends in the housing section 12 provides an air vent for breathing of air into the housing so there will be no vacuum resistance or back up to the free flow of urine therethrough. In the ambulatory position of the females in FIG. 7, the positioning of the collection device is substantially as that described above but the vaginal insert 28 has been incorporated for further stability. Thus, the insert 28 has been assembled to the flange tracks and adjusted therealong for comfortable insertion into the vaginal canal of the particular female. Here again, the device is positioned to encourage urine flow from the ingress to the egress end of the housing. In assembled position, if the combined conduits 40, 42 are urged slightly inwardly of the housing, the orientation of the portion 42 (a portion being cut out at 42a for drainage) will be maintained by the interior configuration of the inclined portion 16 and the light spring 46 will continue to urge the cap 50 into sealing position. As an additional safe guard against detachment or shifting of the collection device from fitted position and perhaps as a sense of security for the female user, a panty brief 72 may be used in conventional manner to further trap or contain the device, thus applying its pressure over the device along the length thereof. The panty is apertured for projection therethrough of the discharge nipple 36 and tube 70 which may be taped to the user as along the thigh area. The panty may also be provided with an opening at the anal area. The panty is shown in FIG. 7 but it is to be understood that it may be similarly applied in the prone position of FIG. 6, if desired.

What is claimed is:

1. A urine collecting device for female subjects, as for incontinent females; comprising a flexible cup-shaped cap for external application in sealing disposition around the urethral orifice, a substantially closed housing which is elongate from forward to rearward ends to be disposed along the uro-genital and labial folds region preventing leakage of urine therealong, conduit means, means supporting said conduit means at the forward end of the housing and permitting movement relative thereto for comfortable fitting and adjustment, said conduit means being in liquid communication with the interior of said cap and the forward end of said housing for directing discharged urine into said housing; the cap, conduit means and housing being relatively small sized and shaped for enclosure of the cap and conduit means and at least partial enclosure of the housing for containment and support thereof by the labial folds in said region; and a discharge connection at the rearward end of the housing for discharge of collected urine therefrom.

2. A device as claimed in claim 1, wherein the conduit means is connected to the cap by a resilient bellows permitting relative adjustment therebetween.

3. A device as claimed in claim 1, wherein the conduit means is resiliently urged outwardly of the housing with said cap.

4. A device as claimed in claim 3, wherein the conduit means is angled within the housing rearwardly thereof for promoting flow of urine therethrough.

5. A device as claimed in claim 4, wherein the portion of the conduit means connected to said cap extends through an opening in the housing to permit air breathing facilitating flow of urine therethrough.

6. A device as claimed in claim 1, wherein the cap is longitudinally oval in shape for snug fitting around the urethral opening.

7. A device as claimed in claim 6, wherein the cap is provided with inner and outer sealing lips for effective sealing against leakage of urine discharge from the urethra.

8. A device as claimed in claim 1, wherein there is provided support means extending from the rearward end of said housing with permission disposition for entrapment thereof in the fourchette area for further stability and support of the device when fitted to the anatomical configuration of the female user.

9. A device as claimed in claim 8, wherein the support means comprises a perineal pad for disposition in the fourchette area.

10. A device as claimed in claim 1, wherein the portion of the conduit means in communication with the cap extends through a housing opening providing air breathing and is resiliently urged outwardly with said cap.

11. A device as claimed in claim 10, wherein the inner end of the conduit means is angled rearwardly within the housing to promote flow of urine therethrough.

12. A device as claimed in claim 11, wherein the interior surface of the housing in the region of the conduit means is complementally shaped relative to the angled portion of the conduit means to maintain the rearward orientation thereof regardless of relative adjustment.

13. A urine collecting device for female subjects, as for incontinent females; comprising a flexible cup-shaped cap for external application in sealing disposition around the urethral orifice, a substantially closed housing which is elongate from forward to rearward ends to be disposed along the uro-genital and labial folds region preventing leakage of urine therealong, conduit means in liquid communication with the interior of said cap and the forward end of said housing for directing discharged urine into said housing; the cap, conduit means and housing being relatively small sized and shaped for enclosure of the cap and conduit means and at least partial enclosure of the housing for containment and support thereof by the labial folds in said region; a discharge connection at the rearward end of the housing for discharge of collected urine therefrom; and said housing being provided with external smooth track formations along its length within the vertical extent thereof at the forward end portion and serving at least in part as surfaces for the labial folds to overlie and engage and for attachment of a support appurtenance.

14. A device as claimed in claim 13, wherein the track formations are inwardly inclined at the rear ends thereof for reduction in transverse width for fitment in the fourchette area of the user for increased stability of the device in use.

15. A device as claimed in claim 13, wherein the housing comprises an interiorly recessed bottom portion joined to a cover portion along flanges forming the track formations which are reduced in transverse width at the rear ends thereof for stabilizing fitment of the device in the fourchette area of the user.

16. A device as claimed in claim 15, wherein the reduced width portion of the track formations carries a perineal pad for entrapment in the fourchette area of the user.

17. A device as claimed in claim 16, wherein a vaginal insert is transversely recessed to complementally engage said track formations for adjustably and removably attaching the insert on the housing for vaginal insertion to give additional stability and support to the device when applied to a user.

18. A device as claimed in claim 17, wherein the recess in the vaginal insert is of a size to clear the perineal pad as the insert is applied to or removed from the housing.

19. A urine collecting device for female subject, as for incontinent females; comprising a flexible cup-shaped cap for external application in sealing disposition around the urethral orifice, a substantially closed housing which is elongate from forward to rearward ends to be disposed along the uro-genital and labial folds region preventing leakage of urine therealong, conduit means in liquid communication with the interior of said cap and the forward end of said housing for directing discharged urine into said housing; the cap, conduit means and housing being relatively small sized and shaped for enclosure of the cap and conduit means and at least partial enclosure of the housing for containment and support thereof by the labial folds in said region; a discharge connection at the rearward end of the housing for discharge of collected urine therefrom, said housing having external smooth track formations along its length and serving at least in part as surfaces for the labial folds to overlie and engage; and a vaginal insert transversely recessed to complementally engage said track formations for adjustably and removably attaching the insert in position on the housing for vaginal insertion to give additional stability and support to the device when applied to a female user.

20. A device as claimed in claim 19, wherein the housing is provided with a perineal pad rearwardly extending therefrom for entrapment in the fourchette area, and wherein the recess in the vaginal insert is of a size to clear the said pad as the insert is applied to or removed from the housing.

* * * * *